(12) United States Patent
Cruz Trabanino

(10) Patent No.: US 12,721,501 B2
(45) Date of Patent: Sep. 1, 2026

(54) MODULAR ENDOSCOPE

(71) Applicant: Sigma Engineering Concepts, LLC, Marysville, WA (US)

(72) Inventor: Carlos J. Cruz Trabanino, Marysville, WA (US)

(73) Assignee: Sigma Engineering Concepts LLC, Marysville, WA (US)

( * ) Notice: Subject to any disclaimer, the term of this patent is extended or adjusted under 35 U.S.C. 154(b) by 192 days.

(21) Appl. No.: 18/629,334

(22) Filed: Apr. 8, 2024

(65) Prior Publication Data

US 2024/0335095 A1 Oct. 10, 2024

Related U.S. Application Data

(60) Provisional application No. 63/457,539, filed on Apr. 6, 2023.

(51) Int. Cl.
*A61B 1/00* (2006.01)
*A61B 1/005* (2006.01)

(52) U.S. Cl.
CPC ...... *A61B 1/00105* (2013.01); *A61B 1/00042* (2022.02); *A61B 1/00101* (2013.01);
(Continued)

(58) Field of Classification Search
CPC ............ A61B 1/00101; A61B 1/00105; A61B 1/00124; A61B 1/00128; A61B 1/00181; A61B 1/005; A61B 1/0052
See application file for complete search history.

(56) References Cited

U.S. PATENT DOCUMENTS 5,665,100 A 9/1997 Yoon
5,682,199 A 10/1997 Lankford
(Continued)

FOREIGN PATENT DOCUMENTS

EP 1769722 A2 * 4/2007 ......... A61B 1/00133
WO WO-2018156059 A1 * 8/2018 ............... A61B 1/04
WO WO-2021127449 A1 * 6/2021 ........... A61B 1/0055

OTHER PUBLICATIONS

"Endoscopic Imaging Technology Today"—Boese et al., Diagnostics 2022, 12, 1262. https://doi.org/10.3390/diagnostics12051262 (Year: 2022).*

(Continued)

*Primary Examiner* — Mainul Hasan
(74) *Attorney, Agent, or Firm* — Bold IP PLLC; Binita Singh

(57) ABSTRACT

A modular endoscope system is described which can allow a single modular endoscope system to perform several imaging and therapeutic procedures. The modular endoscope system includes one or more control sections, one or more insertion tube sections, and one or more head sections that are interchangeable and combinable with respect to an intended endoscopy procedure. These sections may be connected, and signals may transmit electronically between the sections. Further, the modular endoscope system may incorporate a "scope-by-wire" control system for the distal end of the insertion tube section. The one or more control sections, the one or more insertion tube sections, and the one or more head sections of the modular endoscope are interchangeable so that different control, insertion, and head sections can be combined to address the specific needs of a medical procedure.

20 Claims, 8 Drawing Sheets

(52) U.S. Cl.
CPC ...... *A61B 1/00124* (2013.01); *A61B 1/00128* (2013.01); *A61B 1/005* (2013.01)

(56) References Cited

U.S. PATENT DOCUMENTS

| | | | | |
|---|---|---|---|---|
| 6,059,719 | A | 5/2000 | Yamamoto et al. | |
| 7,435,218 | B2 | 10/2008 | Krattiger | |
| 8,419,623 | B2 | 4/2013 | Garcia et al. | |
| 9,107,573 | B2 | 8/2015 | Birnkrant | |
| 10,092,167 | B2 | 10/2018 | Kirma et al. | |
| 10,470,649 | B2 | 11/2019 | Levy et al. | |
| 10,863,889 | B2 * | 12/2020 | Schaaf | A61B 1/012 |
| 2007/0162095 | A1 | 7/2007 | Kimmel et al. | |
| 2007/0213590 | A1 | 9/2007 | Squicciarini | |
| 2008/0214896 | A1 | 9/2008 | Krupa et al. | |
| 2009/0171150 | A1 | 7/2009 | Iede et al. | |
| 2011/0313245 | A1 | 12/2011 | Scholly et al. | |
| 2020/0077874 | A1 | 3/2020 | Long et al. | |
| 2021/0068624 | A1 | 3/2021 | Shin et al. | |
| 2021/0145257 | A1 | 5/2021 | Levinson | |
| 2021/0338045 | A1 | 11/2021 | Crowley | |
| 2023/0070386 | A1 * | 3/2023 | Koubi | A61B 1/00105 |
| 2025/0235085 | A1 * | 7/2025 | Murdeshwar | A61B 1/018 |

OTHER PUBLICATIONS

"Robotic Autonomy for Magnetic Endoscope Biopsy"—Martin et al., IEEE Transactions on Medical Robotics and Bionics, vol. 4, No. 3, Aug. 2022 (Year: 2022).*

* cited by examiner 156
155
155
156
153
151
150
152
130

156
153
155
155
154
151
150
152
130

155
153
155
153
154
151
150
152
130

MODULAR ENDOSCOPE

CROSS-REFERENCE TO RELATED APPLICATIONS

This application is a non-provisional application which claims priority to U.S. Provisional Application No. 63/457, 539 filed on Apr. 6, 2023, which is incorporated by reference in its entirety.

FIELD OF DISCLOSURE

The present invention relates to medical devices, and more specifically to modular endoscopes.

BACKGROUND

An endoscope is a medical device, and more specifically an optical instrument used to look into a body cavity or organ. An endoscope is a long, thin tube which can be inserted into the body to observe an internal organ or tissue in detail. An endoscope can also be used to carry out other important functions, such as and not limited to imaging and minor surgery. Generally, endoscopes are inserted though openings, including the mouth, anus, or small incisions. Endoscopy, which is a procedure using an endoscope, is incredibly useful in many areas of medicine and a huge number of endoscopies are carried out throughout the world due to the minimal invasiveness and few risks during a procedure. Therefore, endoscopes are useful for investigating many systems within the human body.

An example of a procedure using an endoscope is an EGD (esophagogastroduodenoscopy or upper endoscopy). An EDG is a procedure to diagnose and treat problems in the upper GI (gastrointestinal) tract. The endoscope generally has a tiny light and video camera on one end. The tube is put into the mouth and throat. Then it is slowly pushed through the esophagus and stomach, and into the duodenum. The end advancing through the body has the camera so the images may be viewed on a monitor. Often times, images may be collected, and other procedures may need to be performed based on the observation to treat the problem in the GI tract. In such a case, another endoscope which can perform the recommended procedure may be used, and such procedures may involve and not be limited to tissue samples (biopsies), observe tissue abnormalities, remove obstructions, etc. Such procedures may require endoscopes which are structured to provide those functionalities. Often this may require a healthcare provider to invest in several endoscopes to be able to provide the required procedure.

Conventional endoscopes have a high acquisition cost and for a complete set to provide a relatively full range of therapeutic procedures in a specialized field, can significantly increase the cost. There are associated costs for each endoscope within a practice, such as maintenance and continuous training and skills, both for physicians and endoscopy nurses. Considering these disadvantages, there are available solutions in the form of disposable endoscopes. Despite some advantages to the disposable systems, there are drawbacks. These are single use disposable scopes which address some of these problems but fail as far as increasing biohazardous waste disposal and being environmentally unfriendly.

Thus, there still exists a need to improve on the conventional endoscopes and the requirement to acquire multiple endoscopes to address multiple imaging requirements and therapeutic procedures.

SUMMARY

In one or more embodiments described herein, several advantages are presented including cost reduction, simplification of therapeutic procedures available, and versatility of procedures available on one system. The one or more non-limiting embodiments describe a modular endoscope system that includes one or more control sections, one or more insertion tube sections, and one or more head sections. The control section has a distal coupling end that may be coupled to a proximal coupling end on the insertion tube section. The insertion tube section further has a distal coupling end that may be coupled to a proximal coupling end on the head. The coupling ends have electronic contacts that allow the control section, the insertion tube section, and the head section to communicate with each other. The modular endoscope system allows interchangeability between the sections to offer imaging and therapeutic procedure versatility in one system. In other words, one modular endoscope system may be able to perform multiple procedures by interchanging between the available multiple options of the one or more control sections, the one or more insertion tube sections, and the one or more head sections.

Other aspects and advantages of the invention will be apparent from the following description and the appended claims.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

Figure 1:
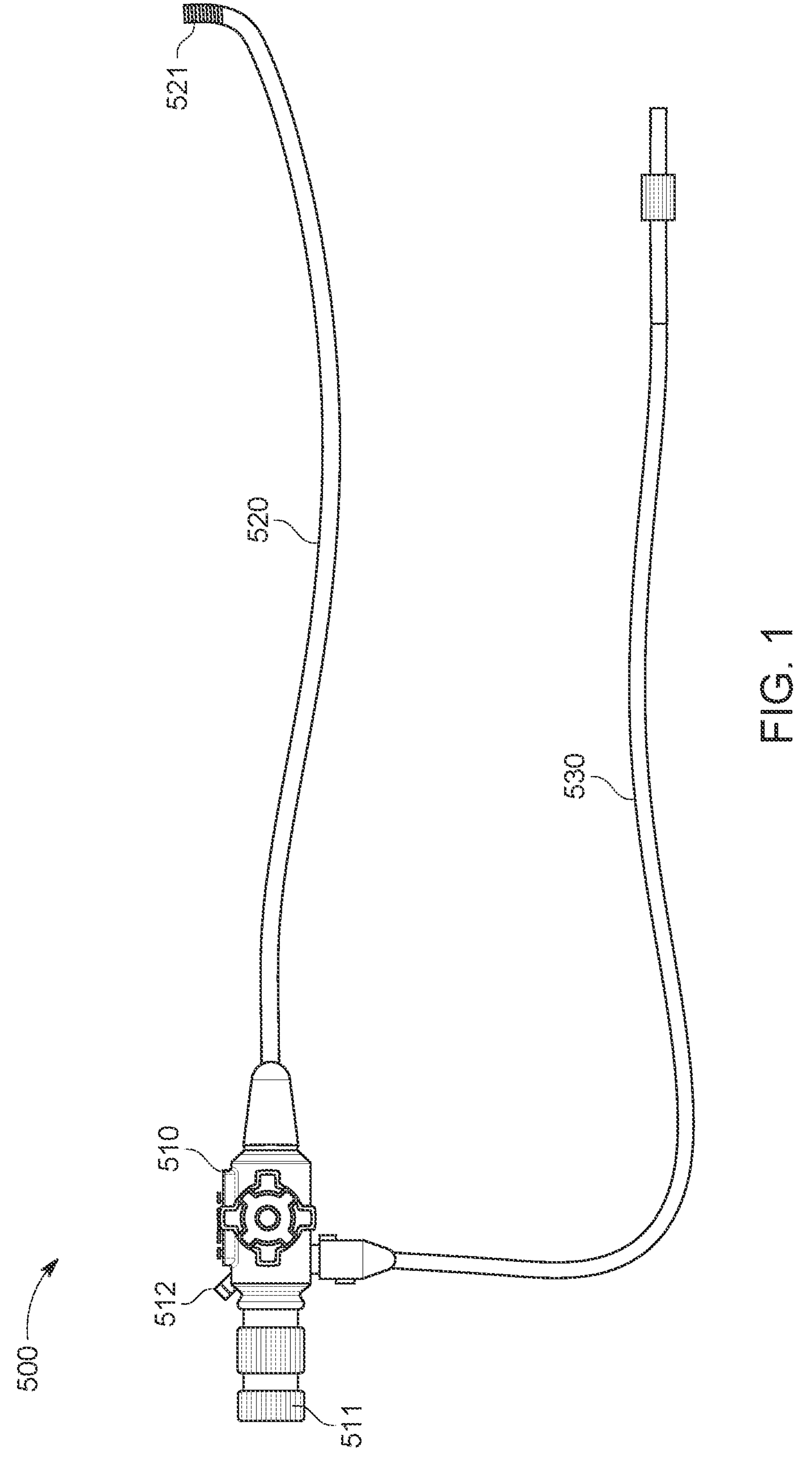
FIG. 1 is a pictorial illustration of a prior art endoscope, a general endoscope.

In the Summary above and in this Detailed Description, and the claims below, and in the accompanying drawings, reference may be made to particular features of the invention. It may be understood that the disclosure of the invention in this specification includes all possible combinations of such particular features. For example, where a particular feature may be disclosed in the context of a particular aspect or embodiment of the invention, or a particular claim, that feature can also be used, to the extent possible, in combination with and/or in the context of other particular aspects and embodiments of the invention, and in the invention generally.

Where reference may be made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

“Exemplary” may be used herein to mean “serving as an example, instance, or illustration.” Any aspect described in this document as “exemplary” may not necessarily be construed as preferred or advantageous over other aspects.

Throughout the drawings, like reference characters are used to designate like elements. As used herein, the term “coupled” or “coupling” may indicate a connection. The connection may be a direct or an indirect connection between one or more items. Further, the term “set” as used herein may denote one or more of any items, so a “set of items” may indicate the presence of only one item or may indicate more items. Thus, the term “set” may be equivalent to “one or more” as used herein.

With reference to FIG. 1, FIG. 1 is an illustration of an example of a prior art endoscope 500. The prior art endoscope 500 comprises of a control body 510, an insertion tube 520, and a universal tube 530. The control body 510 may comprise an eye piece or video controls 511. The control body 510, the insertion tube 520, and the universal tube 530 are typically integrated as a single piece wherein these parts are not removable or interchangeable. The insertion tube 520 includes a flexible tip 521. The flexible tip 521 is a part of the insertion tube 520, which further includes an optic lens, a light guide, a biopsy channel, and an air/water nozzle. A typical endoscope as shown in this example of the prior art endoscope 500 may have glass fiber bundles (not shown) in the insertion tube 520 to transmit a picture back to the eyepiece 511 or a camera (not shown) though the video controls. An opening 512 for wires or instruments may be included in the control body 510 (as shown in FIG. 1) or may also be included in the insertion tube 520. Overall, a typical endoscope is a single unit wherein the parts are not interchangeable and generally cannot be modified to accommodate different procedures. Specific endoscopes vary based on their requirements and thus one endoscope is generally not usable for use in most all procedures.

The invention described herein provides for an improved modular endoscope system which can allow a single modular endoscope system to perform several imaging and therapeutic procedures as described in one or more non-limiting embodiments.

The present disclosure describes one or more embodiments of a modular endoscope system that may include one or more control sections, one or more insertion tube sections, and one or more head sections. These sections may be connected and transmit electronically. Further, the modular endoscope system may incorporate a “scope-by-wire” control system for the distal end of the insertion tube section, instead of the current direct-driven pulley system. The one or more control sections, the one or more insertion tube sections, and the one or more head sections of the modular endoscope are interchangeable so that different control, insertion, and head sections can be combined to address the specific needs of a medical procedure. The different sections may interface with each other using a sealed bayonet-type locking system and have pin matching electronic contacts to communicate with each other. The one or more control sections would contain the user interface elements as well as the main processing electronics and power supply. The one or more insertion tube sections would have the mechanics for the wiring connecting the control section to a chosen head section based on the medical procedure to be performed. The one or more head sections would each have a purpose-selected head depending on the procedure to be performed and would contain one or more optics, one or more lighting system, an air and water nozzle, one or more work channels, and other specialty systems required for a chosen procedure.

Figure 2:
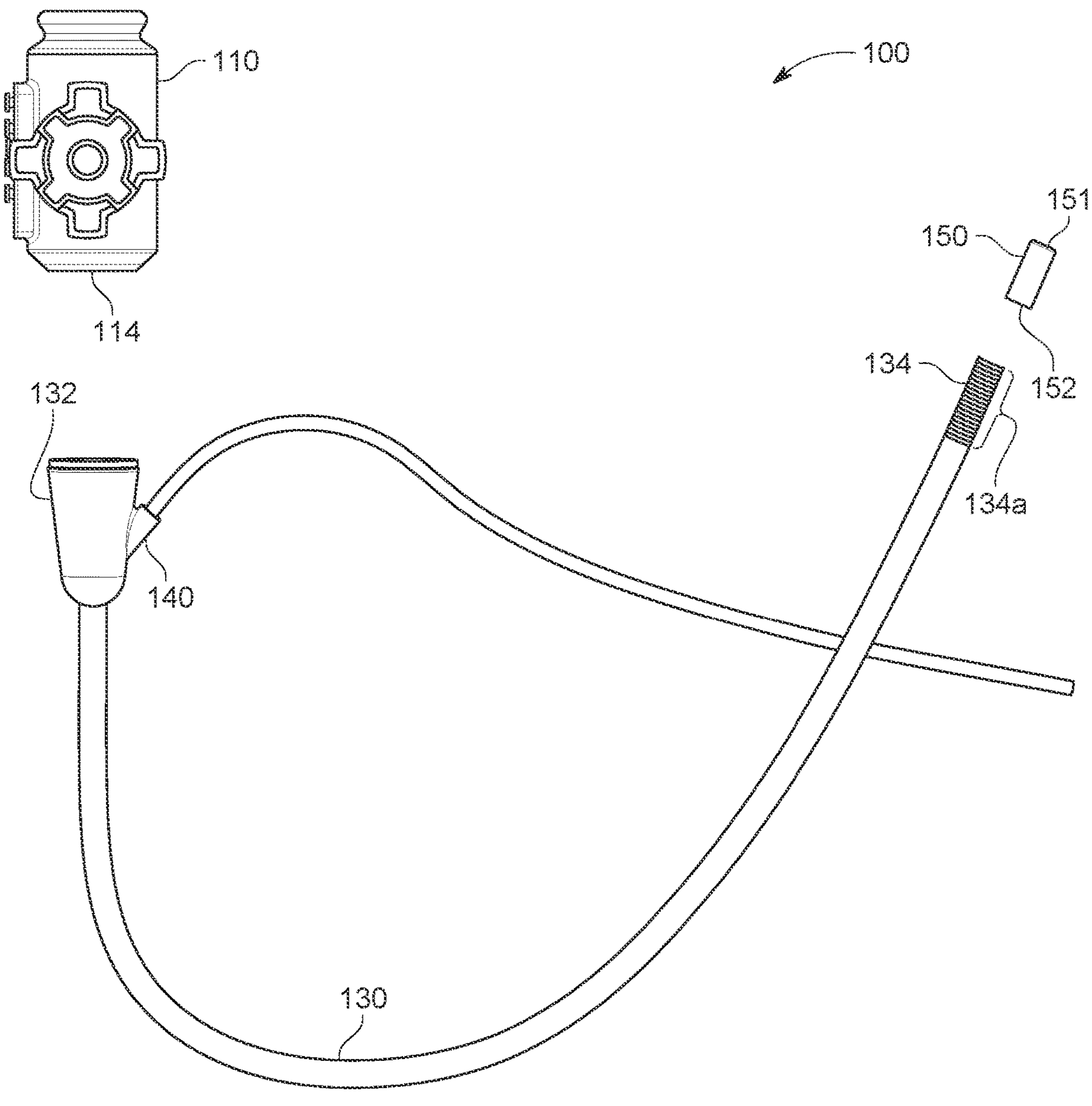
FIG. 2 is a pictorial illustration of a modular endoscope system shown in a disassembled view in accordance with an illustrative embodiment.
Figure 3:
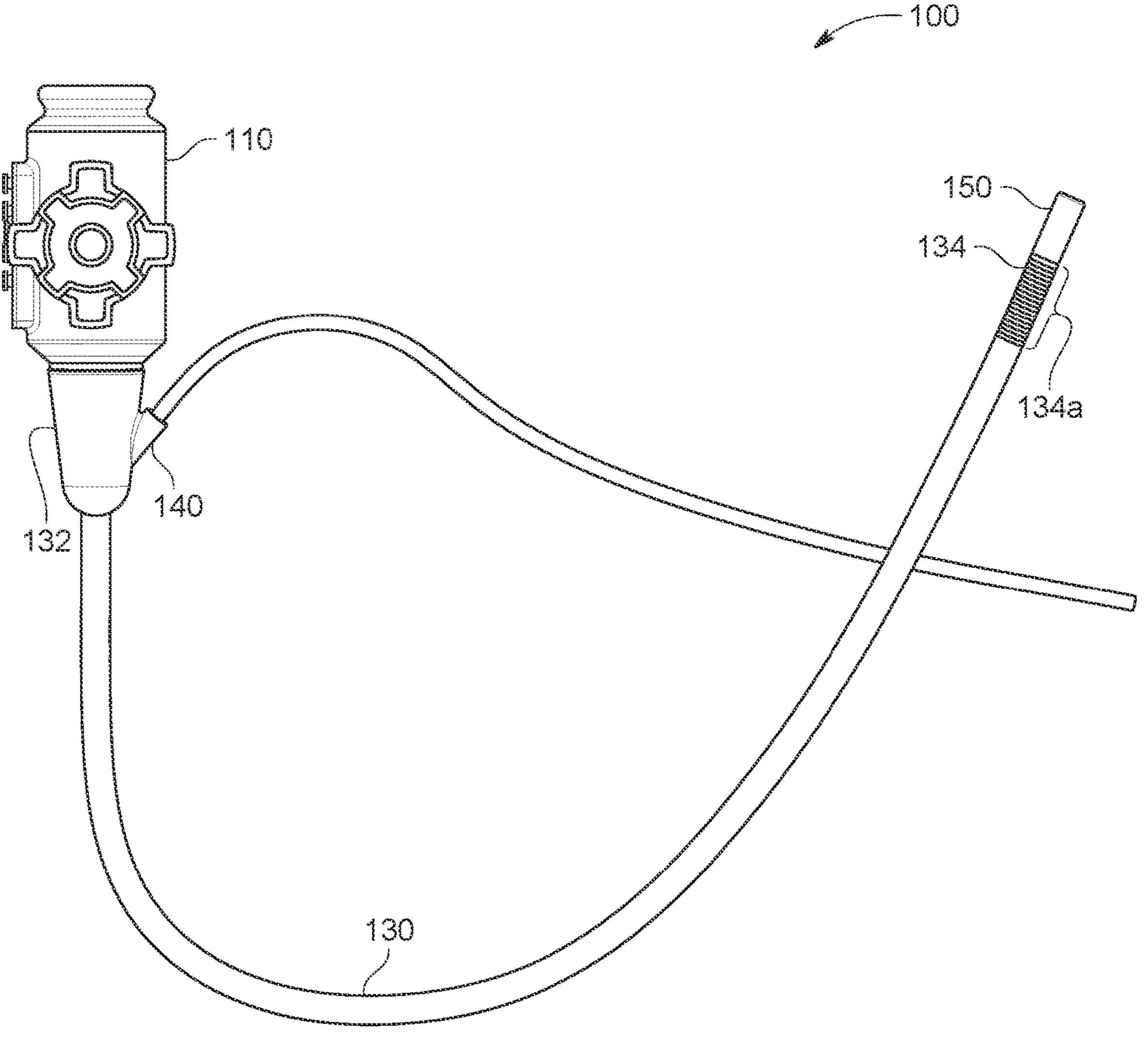
FIG. 3 is a pictorial illustration of the modular endoscope shown in an assembled view in accordance with an illustrative embodiment.

With reference to FIGS. 2 and 3, an illustration of a modular endoscope 100 is shown that is composed of multiple sections chosen depending on the intended purpose. FIG. 2 illustrates an exploded view of the modular endoscope 100, and FIG. 3 illustrates the modular endoscope 100 combined with the separate sections for use. The modular endoscope 100 includes one or more control sections 110, one or more insertion tube sections 130, and one or more head sections 150. The modular endoscope 100, as shown in FIGS. 2 and 3, is intended to be put together by selecting a single control section 110, a single insertion tube section 130, and a single head section 150, which are selected depending on an intended case of application. The control section 110, the tube section 130, and the head section 150 are adjoined together to perform the intended purpose(s). Thus, the present disclosure of the modular endoscope 100 is provided so that a plurality of endoscopy applications is covered with the availability of one or more of each of the control, insertion tube, and head sections allowing the possibility of combining the appropriate sections of each depending on the case of application.

One or more embodiments of the insertion tube section 130 are best seen in FIGS. 2 and 3. The insertion tube section 130 has a proximal end 132 and a distal end 134, wherein both ends have connection capabilities to the one or more control section 110 and the one or more head sections 150. One non limiting example of a connection mechanism is via a bayonet mount. The proximal end 132 of the insertion tube section 130 connects with a distal end 114 of the control section 110; the distal end 134 of the insertion tube section

130 connects with a proximal end 152 of the head section 150. In the schematic, it is shown that the proximal end 132 of the insertion tube section 130 is wider than the distal end 134 as the proximal end 132 connects with the control section 110 and is not inserted into an opening of a body cavity or incision. Additionally, one or more working channel entry ports and one or more air/water/suction ports may also be configured on the insertion tube section 130, in proximity to the proximal end 132.

The modular endoscope 100 may be designed with one or more accessory ports 140. As an example, shown in FIGS. 2 and 3, a single insertion port 140 is configured onto the insertion tube section 130. The insertion port allows access for introducing air, water, suction means, and acts as a work channel. It is to be understood, that the modular endoscope 100 may include more than one accessory port, to provide separate access for air/water, and possibly two work channels. Other arrangements are also within the disclosure of the modular endoscope 100.

Figure 4:
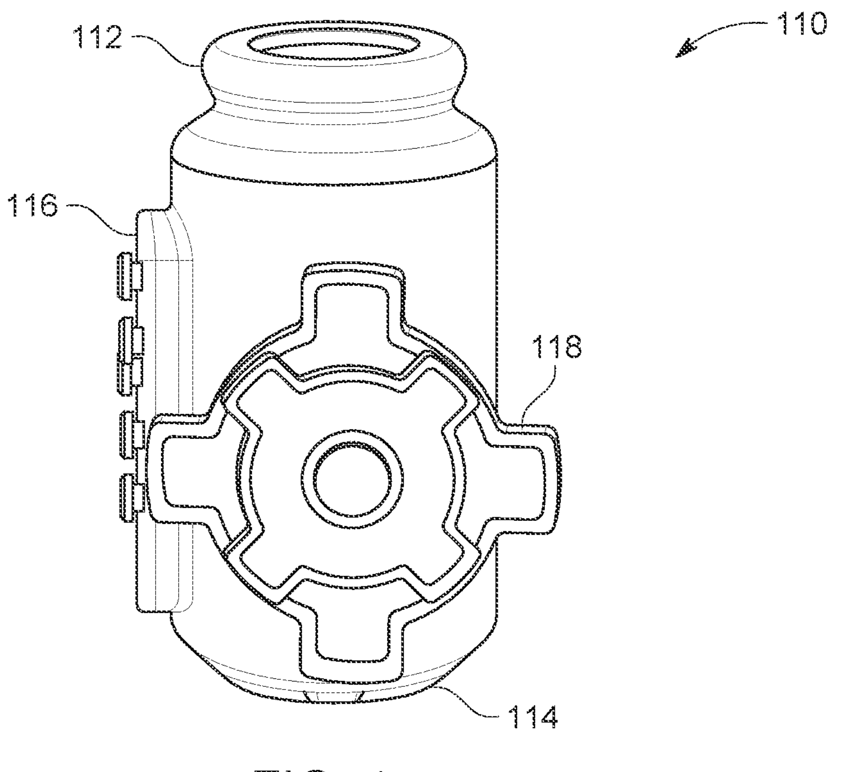
FIG. 4 is a pictorial illustration of a front view of a control section of the modular endoscope in accordance with an illustrative embodiment.
Figure 5:
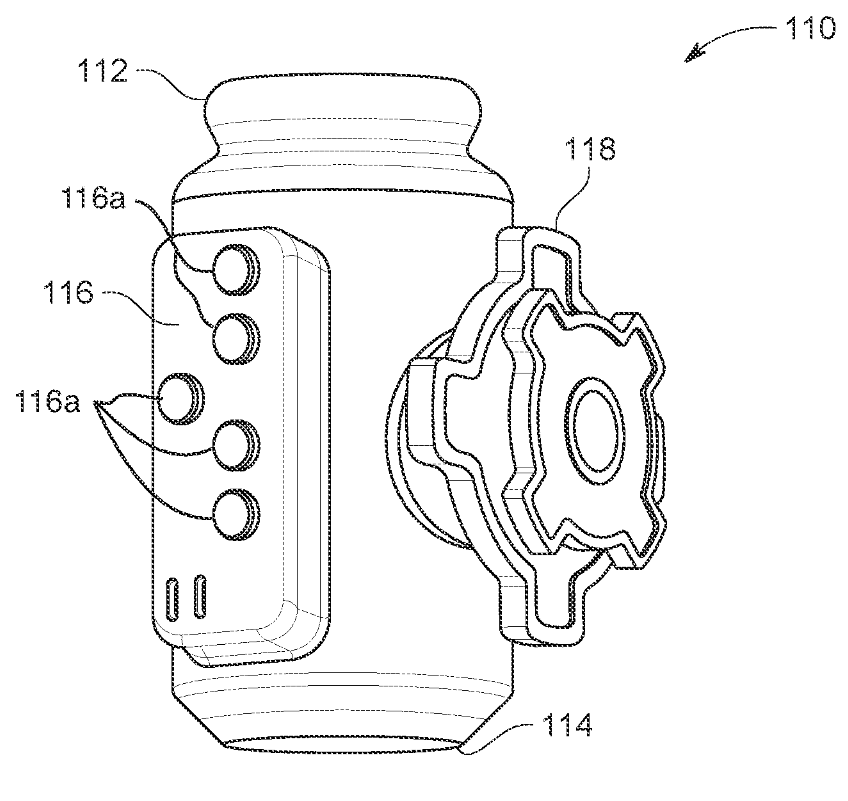
FIG. 5 is a pictorial illustration of a side of the control section shown in FIG. 4 in accordance with an illustrative embodiment.

FIGS. 4 and 5 illustrate the control section 110 according to one or more embodiments. In the illustrated embodiment, the control section 110 is shown to have a proximal end 112 and a distal end 114, wherein the proximal end 112 has an electronic viewfinder, and the distal end 114 has a mounting feature, such as a bayonet mount. The bayonet mount on the distal end 114 allows the connection between the control section 110 and the proximal end 132 of the insertion tube section 130, which may have a corresponding bayonet mount (see FIG. 8, bayonet mount at the proximal end 132). Additionally, the linking of the control section 110 to the insertion tube section 130 would include all necessary electrical contacts for signal and power delivery, such as electrical contacts 133 shown in FIG. 8 on the insertion tube proximal end 132. Similar contacts would be included on the distal end 114 of the control section 110.

The control section 110 may further include a control panel 116 on an outside surface of the control section 110. Essentially, the control section 110 may be responsible for operating most functions of the modular endoscope 100. The control section 110 may include and not be limited to software, input/output ports, power delivery, firmware, and human interface controls such as fine control buttons and other multifunction control buttons. The fine control buttons and multifunctional control buttons are collectively shown as control buttons 116*a*. These input/output ports and the human interface controls may be included on the control panel 116 and be easily accessible for use. In one or more non-limiting embodiments, the main input/output interface may be a USB-C connector, which is capable of transmitting both data and power on a single cable. Essentially, the USB-C connector allows for both power delivery and for simultaneous video broadcasting to a monitor. The human interface controls on the control panel 116 may include multifunction control buttons that are reprogrammable such that the buttons may be programmed depending on which insertion tube section 130 and which head section 150 are attached. Additionally, the fine control button may be used for a scope-by-wire system for control of a flexible section (see FIGS. 2 and 7, flexible section 134*a*).

Figure 7:
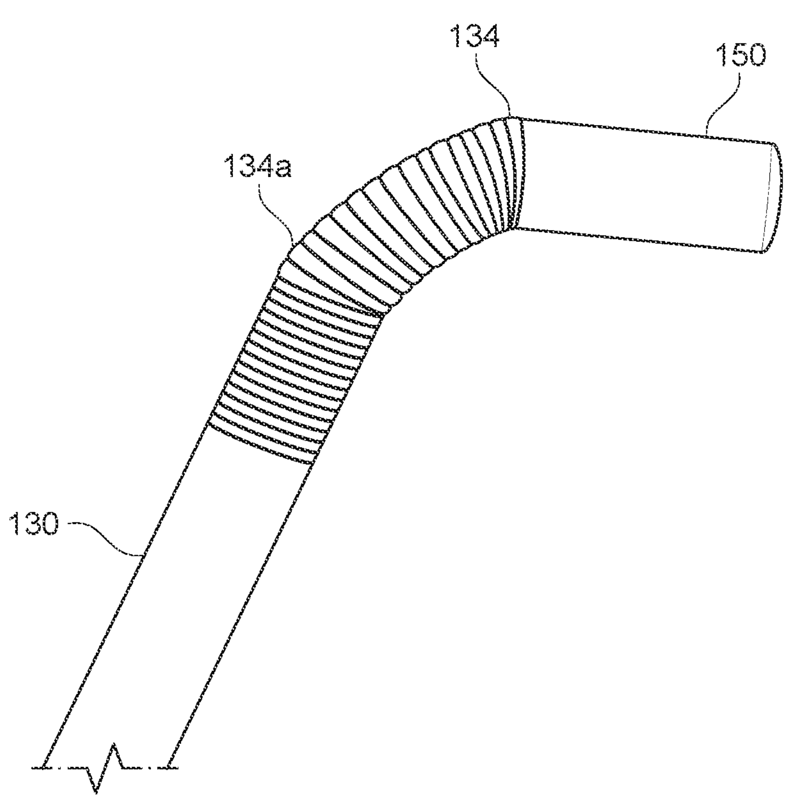
FIG. 7 is a pictorial illustration of a flexible section of the insertion tube section connected with a head section in accordance with an illustrative embodiment.

The control section 110 may also include one or more control knobs 118, as shown for example in FIG. 4, which may be integrated on an outside surface of the control section 110, connected with the relative functioning mechanics on an inside. The control knobs 118 may be configured with potentiometers to control the flexible section 134*a* on a distal end 134 of the insertion tube section 130. FIG. 7 illustrates a movement of the flexible section 134*a*. Thus, the flexible section 134*a* may be controlled via the control knobs 118. It is to be understood that the control knobs 118 may be integrated with functioning systems to move the flexible section 134*a*, such as and not limited to a mechanical pulley system. Other alternative functioning systems to move the flexible section 134*a* are also contemplated within this disclosure.

Figure 8:
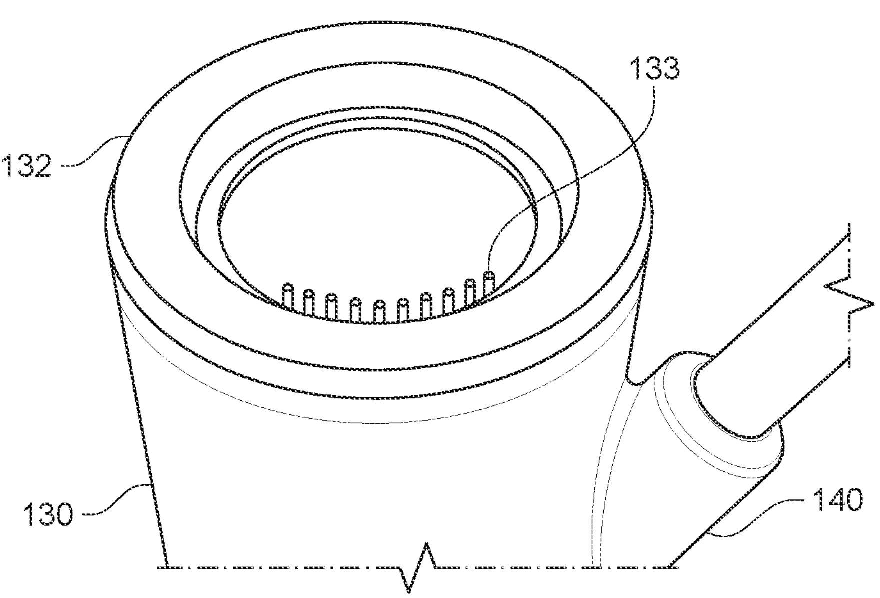
FIG. 8 is a pictorial illustration of a proximal end of the insertion tube section of the modular endoscope system in accordance with an illustrative embodiment.
Figure 9:
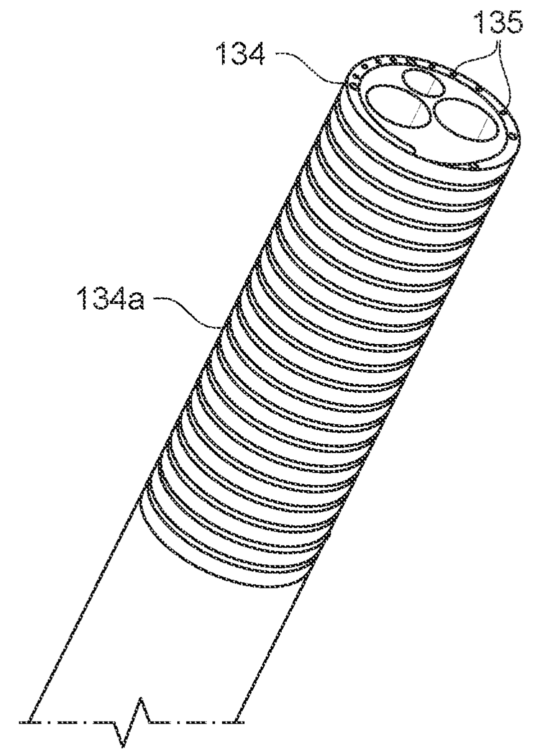
FIG. 9 is a pictorial illustration of a distal end of the insertion tube section that connects with the head section of the modular endoscope system in accordance with an illustrative embodiment.

The bayonet mounts on each of the ends of the insertion tube section 130 and the distal end 114 of the control section 110 include all the necessary electrical contacts. Electrical contacts 133, 135 are shown in FIGS. 8 and 9 on the insertion tube proximal and distal end 132, 134, respectively. Similar electrical contacts are included on the distal end 114 of the control section 110 within the mounting section. The electrical contacts on the control section 110 align and contact the corresponding electrical contacts 133 on the proximal end 132 of the insertion tube section 130 shown in FIG. 8. Additionally, the bayonet mounts on the proximal and distal ends 132, 134 of the insertion tube section may also include the appropriate cavities such as, and not limited to, work channels, air/water/suction lines, among others.

Figure 6:
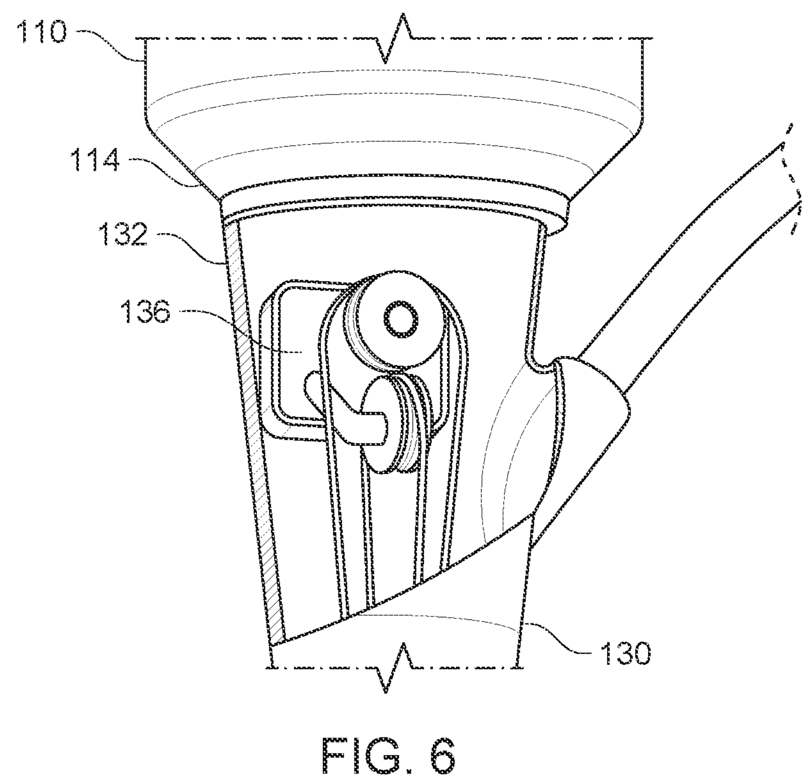
FIG. 6 a pictorial illustration of an internal view of a proximal portion of an insertion tube section of the modular endoscope system in accordance with an illustrative embodiment.

FIG. 6 illustrates an internal view of the proximal end 132 of the insertion tube section 130. The illustration depicts that the insertion tube section 130 is incorporated with one or more servo motors 136 that move a mechanical pulley system that actuates the proximal end 134 of the insertion tube section 130. The distal end 134 of the insertion tube section 130 with the flexible section 134*a* is flexible and may also be referred to as a flexible end. The control section 110 delivers the power for the one or more servo motors 136. Additionally, the control section 110 also delivers a pass-through power for the head section 150. The flexible section 134*a* may function through the mechanical pulley system, wherein the mechanical pulley system is operated through the one or more servo motors 136. The one or more servo motors 136 may operate from any valid electrical control signal, such as and not limited to the control knobs 118, VR (virtual reality) headsets, and remote operators linked through the USB-C connector on the control section 110.

Figure 10:
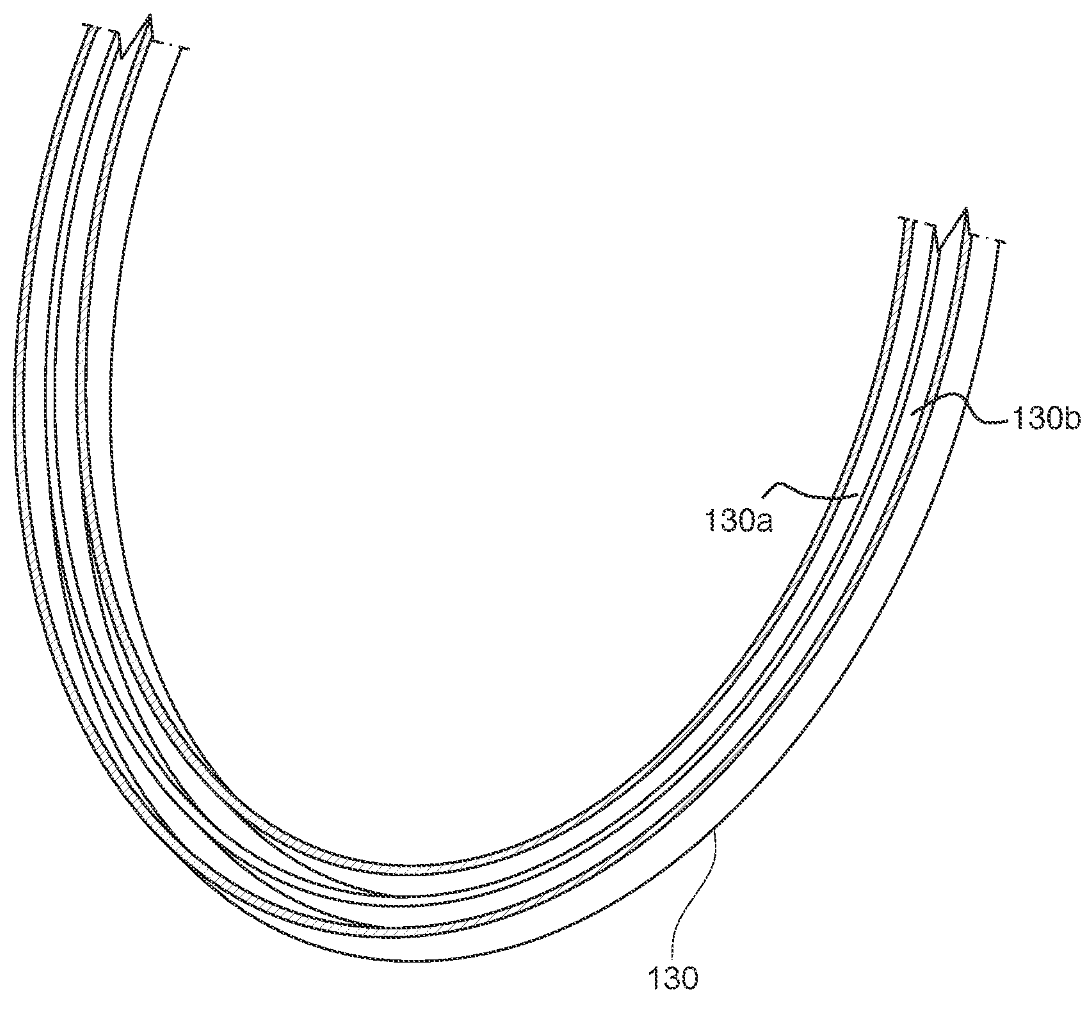
FIG. 10 is a pictorial illustration of a cross-sectional view of an example of the insertion tube section of the modular endoscope system in accordance with an illustrative embodiment.

There may be several variations to the insertion tube section 130 based on the intended procedure. In one or more embodiments, the insertion tube section 130 may be of a standard length. In an alternate embodiment, the insertion tube section 130 may include at least two work channels (e.g. as shown in FIG. 10, insertion tube section 130 with two channels), which would be matched with a corresponding head section 150 having the same number of work channels. In an alternate embodiment, the insertion tube section 130 may have a longer length. An example of a procedure requiring a longer length insertion tube section may include a procedure to reach the small intestine in an adult. In an alternate embodiment, the insertion tube section 130 may have a shorter length than the standard length. An example use of such would be in a procedure requiring exploration of the upper GI (gastrointestinal) tract with more maneuverability. In an alternate embodiment, the insertion tube section 130 may have a smaller diameter for pediatric use. Additionally, the pediatric use insertion tubes may have variations based on a length of the insertion tube section and the number of work channels, and other variations with respect to the applications intended.

Figures 11A, 11B, 11C:
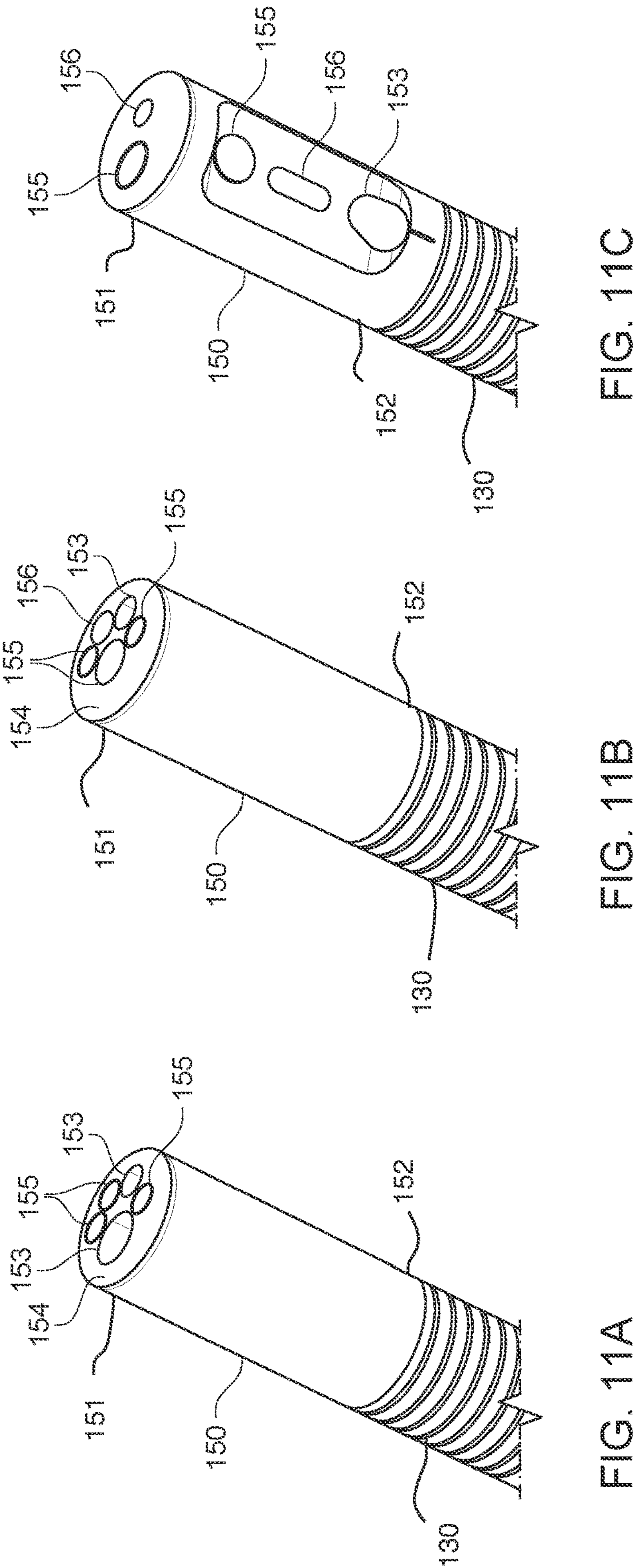
FIG. 11A is a pictorial illustration of an example of a head section having certain capabilities for endoscopy procedures in accordance with an illustrative embodiment.
FIG. 11B is a pictorial illustration of another example of a head section having certain capabilities for endoscopy procedures in accordance with an illustrative embodiment.
FIG. 11C is a pictorial illustration of another example of a head section having certain capabilities for endoscopy procedures in accordance with an illustrative embodiment.

FIGS. 11A to 11C illustrate a perspective view of a distal end 154 of several examples of the head section 150, respectively. The proximal end 152, as shown in FIG. 2, of the head section would also include the bayonet system to connect with the distal end 134 of the insertion tube section 130. The bayonet mount on the proximal end 152 of the head section 150 may include the one or more signal channels, one or more work channels, and one or more lines for air, water, and suction. The bayonet mount on the proximal end 152 may also include the electrical contacts 156 which interact with the electrical contacts on the distal end 134 of the insertion tube section 130 so the required power may be provided to the respective functioning elements on the head section 150. The functioning elements are preferably positioned at the distal end 154 of the head section 150 and may be actuated by the control panel 116 on the control section 110. For example, the head section may include the LED lights and a camera that may be actuated from the control section 110.

As shown in FIGS. 11A to 11B, the head section 150 of the modular endoscope 100 is interchangeable and may include several variations adapted to be connected with a corresponding insertion tube section 130 which in turn is connected with the control section 110. As discussed above, the control buttons 116*a* on the control panel 116 are reprogrammable based on the chosen insertion tube section 130 and the head section 150 so that the appropriate functions may be performed with respect to the applications intended.

In one or more embodiments, the head section 130 may be integrated with the standard features including a single HD/4K camera, a single work channel, an air/water nozzle, and a single LED light. Such an embodiment may be usable for most applications.

In an alternate embodiment, and example of which is shown in FIG. 11B, a multi-camera head may be designed. In this non-limiting embodiment, a camera pack may include two or more focal length HD/4K cameras 155 for wide angle exploration and telephoto views for high-definition views of areas of interest. The embodiment may also include a single work channel and air/water nozzle 153, a front facing LED light 156, and a LED ring light 154.

In an alternate embodiment, an example of which is shown in FIG. 11C, a head section with a side view is designed. This embodiment may include a single forward-facing HD/4K camera 155 and a forward-facing LED light 156. Additionally, one or more work channels and an air/water nozzle 153, a side-facing HD/4 k camera 155*a*, and a side facing LED light. An example use of such a specialized head would be in an exploration which more specifically would allow the view and manipulation of along a side of a gastric esophageal sphincter. Such a head would eliminate the need to make a J-maneuver to view a rear portion as the insertion tube with the head is progressed forward.

In an alternate embodiment, an ERCP (Endoscopic retrograde cholangiopancreatography) head may be designed for use, an example of which is shown in FOG. 10C. ERCP is a technique that combines the use of endoscopy and fluoroscopy to diagnose and treat certain problems of the biliary or pancreatic ductal systems. This embodiment may include a single forward-facing HD/4K camera 155, one forward-facing LED light 156, one side-facing HD/4K camera 155*a*, one side-facing LED light 156*a*, and one side-facing work channel 153*a* for pancreatic probing. This embodiment is similar to existing ERCP endoscopes but includes a forward-facing camera so that a forward-facing view is still visible. Switching between forward-facing and side-facing cameras could be easily accomplished by use of the reprogrammable controls in the control section 110.

In an alternate embodiment, an ultrasound head is designed for use. This embodiment includes a single HD/4K camera, a LED ring light, and an ultrasound emitter and receiver. There are single endoscopes that are built for this purpose, whereas the modular endoscope 100 of the present disclosure provides an option to include this as an interchangeable head rather than purchasing an entire new system.

In an alternate embodiment, a head section with a rear view is designed. This embodiment may include a single forward-facing HD/4K camera, a forward-facing LED light, an air/water nozzle, a work channel, a rear-facing HD/4 k camera, and a rear facing LED light. An example use of such a specialized head would be in the exploration of the stomach and the esophagus, and more specifically would allow the view of a top side of the gastric sphincters or the esophageal sphincter. Such a head would eliminate the need to make a J-maneuver to view a rear portion as the insertion tube with the head is progressed forward.

In an alternate embodiment, a PDM (payload delivery module) head is designed for use. This embodiment may include a forward-facing HD/4K camera, a forward-facing LED light, an air/water nozzle, a side facing camera, a side facing LED light, and a PDM. The PDM may use a compressed air ampule and an injector to deliver medication or contrast dye directly to one or more targeted areas.

An alternate embodiment may include a head section designed with a LiDAR sensor. This embodiment may include a HD/4K camera, a LED ring light, an air/water nozzle, and one LiDAR sensor. The head section designed with a LiDAR sensor may allow for 3D surveying of features to look for suspected cancerous growths, polyps, or other visible abnormalities. The LiDAR sensor may scan a suspected feature and upload the corresponding data to a software system where an accurate 3D representation of the feature(s) is generated allowing precise measurement and comparison to previous measurements taken.

It is to be understood that these are not an exhaustive list of possible variations that can be designed into the unteachable head section. Additional features that are beneficial for an intended application can also be incorporated into a head system for use.

Thus, the modular endoscope system as described above is an interchangeable system which includes one or more control sections, one or more insertion tube sections, and one or more head sections, wherein the sections can be chosen and combined for use with the intended application. The modular endoscope system provides a single unit which can be combined in multiple ways for the intended applications and eliminates the need for a healthcare provider or system to incorporate several single-purpose use endoscopes in their practice.

The corresponding structures, materials, acts, and equivalents of any means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention, according to one or more embodiments described in the present description, may be practiced with modification and alteration within the spirit and scope of the appended claims. Thus, the description is to be regarded as illustrative instead of restrictive of the present invention.

What is claimed is:

1. An apparatus comprising:

a modular endoscope system, comprising:

one or more control sections configured to receive power and transfer data, wherein each of the one or more control sections is configured with a different control interface, processing configuration, or control functionality relative to another of the control sections of the one or more control sections;

one or more insertion tube sections with a flexible tip, wherein each of the one or more insertion tube sections has a different mechanical, dimensional, or channel configuration relative to another of the insertion tube sections of the one or more tube sections;

one or more head sections, wherein each of the one or more head sections has a different imaging, sensing, or therapeutic functionality relative to another of the head sections of the one or more head sections;

wherein a functioning unit is configured by combining a single control section of the one or more control sections, a single insertion tube section of the one or more insertion tube sections, and a single head section of the one or more head sections and wherein each of the one or more control sections, one or more insertion tube sections, and one or more head sections are configured as a standalone module to be selectively interchangeable.

2. The apparatus of claim 1, wherein the one or more control sections, the one or more insertion tube sections, and the one or more head sections are each interchangeable and the functional unit is configured with a combination of the single control section, insertion tube section, and head section based on an intended endoscopy procedure.

3. The apparatus of claim 1, wherein:

a distal end of each of the one or more control sections includes a mounting mechanism and electrical contacts;

a proximal end and a distal end of each of the one or more insertion tube sections include a mounting mechanism and electrical contacts;

a proximal end of each of the one or more head sections includes a mounting mechanism and electrical contacts; and wherein the functioning unit is configured by connecting the mounting mechanism of the single control section with the mounting mechanism on the proximal end of the single insertion tube and connecting the mounting mechanism on the distal end of the single insertion tube with the mounting mechanism on the proximal end of the head section.

4. The apparatus of claim 3, wherein the mounting mechanism on each of the one or more control section, one or more insertion tube sections, and the one or more head sections is a bayonet mount.

5. The apparatus of claim 3, wherein the electrical contacts on each of the single control section, the single insertion tube section, and the single head section comprising the functional unit, deliver power and signal to operate the functional unit.

6. The apparatus of claim 1, wherein each of the one or more control sections includes a control panel and one or more control knobs, wherein:

the control panel includes reprogrammable multifunctional buttons, one or more input and output ports, and a fine control button for fine movement of the flexible tip at the distal end of the insertion tube section; and the one or more control knobs include potentiometers, wherein the one or more control knobs electrically control the flexible tip of the insertion tube section.

7. The apparatus of claim 6, wherein the input/output port includes a USB-C interface for signal, power delivery, and firmware updates.

8. The apparatus of claim 1, wherein a proximal end of each of the one or more insertion tube sections includes a housing for a mechanical pulley system which operates through one or more servo motors which are in electrical contact with the connected single control section of the one or more control sections on the functional unit.

9. The apparatus of claim 1, wherein the one or more head sections comprise one or more optics, one or more lighting system, an air and water nozzle, and/or one or more work channels.

10. The apparatus of claim 1, wherein each of the one or more insertion tubes is integrated with one or more accessory ports for introducing air, water, suction, and/or as a port for a work channel.

11. An apparatus comprising:

a modular endoscope system, comprising:

one or more control sections including user interface controls, power delivery, software, and firmware, wherein each of the one or more control sections is configured with a different control interface, processing configuration, or control functionality relative to another of the control sections of the one or more control sections;

one or more insertion tube sections including a flexible tip, at least one working channel, and further including an air, water, and a suction line, wherein each of the one or more insertion tube sections has a different mechanical, dimensional, or channel configuration relative to another of the insertion tube sections of the one or more tube sections;

one or more head sections, wherein each of the one or more head sections has a different imaging, sensing, or therapeutic functionality relative to another of the head sections of the one or more head sections;

wherein a functioning unit is configured by combining a single control section of the one or more control sections, a single insertion tube section of the one or more insertion tube sections, and a single head section of the one or more head sections; and wherein each of the one or more control sections, one or more insertion tube sections, and one or more head sections are configured as a standalone module to be selectively interchangeable.

12. The apparatus of claim 11, wherein the one or more control sections, the one or more insertion tube sections, and the one or more head sections are each interchangeable and the functional unit is configured with a combination of the single control section, insertion tube section, and head section based on an intended endoscopy procedure.

13. The apparatus of claim 11, wherein:

a distal end of each of the one or more control sections includes a mounting mechanism and electrical contacts;

a proximal end and a distal end of each of the one or more insertion tube sections include a mounting mechanism and electrical contacts;

a proximal end of each of the one or more head sections includes a mounting mechanism and electrical contacts; and wherein the functional unit is configured by connecting the mounting mechanism of the single control section with the mounting mechanism on the proximal end of the single insertion tube and connecting the mounting mechanism on the distal end of the single insertion tube with the mounting mechanism on the proximal end of the head section.

14. The apparatus of claim 13, wherein the mounting mechanism on each of the one or more control section, one or more insertion tube sections, and the one or more head sections is a bayonet mount.

15. The apparatus of claim 13, wherein the electrical contacts on each of the single control section, the single insertion tube section, and the single head section comprising the functional unit, deliver power and signal to operate the functional unit.

16. The apparatus of claim 11, wherein the user interface elements on each of the one or more control sections are included on a control panel and one or more control knobs, wherein:

the control panel includes reprogrammable multifunctional buttons, one or more input and output ports, and a fine control button for fine movement of the flexible tip at the distal end of the insertion tube section; and the one or more control knobs include potentiometers, wherein the one or more control knobs electrically control the flexible tip of the insertion tube section.

17. The apparatus of claim 16, wherein the input/output port includes a USB-C interface for signal, power delivery, and firmware updates.

18. The apparatus of claim 11, wherein a proximal end of each of the one or more insertion tube sections includes a housing for a mechanical pulley system which operates through one or more servo motors which are in electrical contact with the connected single control section of the one or more control sections on the functional unit.

19. The apparatus of claim 11, wherein the one or more head sections comprise one or more optics, one or more lighting system, an air and water nozzle, and/or one or more work channels.

20. The apparatus of claim 11, wherein each of the one or more insertion tubes is integrated with one or more accessory ports for introducing air, water, suction, and/or as a port for a work channel.

* * * * *